United States Patent [19]

Matsunaga et al.

[11] 4,271,322
[45] Jun. 2, 1981

[54] PROCESS FOR PREPARATION OF PHENOLS

[75] Inventors: Fujihisa Matsunaga; Hirohiko Nambu, both of Iwakuni, Japan

[73] Assignee: Mitsui Petrochemical Industries, Ltd., Tokyo, Japan

[21] Appl. No.: 109,214

[22] Filed: Jan. 3, 1980

[30] Foreign Application Priority Data

Jan. 11, 1979 [JP] Japan .................................. 54-1012

[51] Int. Cl.³ ........................ C07C 37/08; C07C 37/74
[52] U.S. Cl. .................................. 568/798; 568/741; 568/749
[58] Field of Search ................ 568/798, 768, 741, 754

[56] References Cited

U.S. PATENT DOCUMENTS

| 3,331,755 | 7/1967 | Neuworth | 568/756 |
| 3,978,141 | 8/1976 | Jourffret | 568/798 |
| 4,158,611 | 6/1979 | Cooke | 568/754 |

FOREIGN PATENT DOCUMENTS 1411730  10/1975  United Kingdom ..................... 568/754

Primary Examiner—Werren B. Lone
Attorney, Agent, or Firm—Sherman & Shalloway

[57] ABSTRACT

Disclosed is a process for the preparation of phenols which comprises the steps of (I) decomposing a hydroperoxide of an isopropyl aromatic compound with an acid catalyst, (II) separating the decomposition product obtained in step (I) into acetone, phenols, hydrocarbons and distillation residue by distillation of the decomposition product and (III) thermally decomposing the distillation residue and recycling the resulting crude phenol to step (II), wherein the crude phenol obtained in step (III) is contacted with a glycol to form a hydrocarbon layer and an extract layer comprising the glycol and phenol, and the phenol in said extract layer is recycled to step (II).

According to this process, mingling of impurity components having a boiling point close to that of the desired phenol, which are contained in the thermal decomposition product of the distillation residue, into the product phenol can be effectively prevented, and the desired phenol can be obtained at a high purity and at a high recovery yield.

6 Claims, 3 Drawing Figures

PROCESS FOR PREPARATION OF PHENOLS

BACKGROUND OF THE INVENTION

(1) Field of the Invention

The present invention relates to a process for preparing phenols from hydroperoxides of isopropyl aromatic compounds. More particularly, the invention relates to a process for recovering phenols having a high purity at a high efficiency.

(2) Description of the Prior Art

Processes for the preparation of phenols such as phenol and cresol comprising oxidizing an isopropyl aromatic compound such as cumene or cymene with molecular oxygen to form a hydroperoxide and acid-decomposing the hydroperoxide have been known in the art. Phenols, acetone simultaneously formed, unreacted hydrocarbons and by-products such as α-methylstyrene can be isolated by distillation of acid-decomposition products. The distillation residue is composed of polycondensates of various components, and phenols and other valuable components can be obtained by thermal decomposition of this distillation residue. For recovery of phenols from such thermal decomposition product, there is ordinarily adopted a process in which a distillable fraction of the thermal decomposition product is returned to the system for distillation of the acid-decomposition product and phenols contained in this fraction are recovered together with phenols contained in the acid-decomposition product. However, since compounds having a boiling point close to those of phenols are formed at the thermal decomposition, if the above-mentioned fraction of the thermal decomposition product is returned to the distillation system as described above, mingling of impurities cannot be avoided, resulting in reduction of the purity of recovered phenols and discoloration of the products. In order to prevent or eliminate these disadvantages, the load of the distillation column should be increased. Furthermore, another disadvantage is that the recovery ratio of phenols in the distillation column can hardly be maintained at a high level. More specifically, when phenol is prepared, for example, according to the cumene process, if the distillation residue is thermally decomposed, not only phenol but also by-products having a boiling point close to that of phenol, for example, phenylbutenes and 2-methyl-4-phenylpentenes are included in the thermal decomposition product. If this thermal decomposition product is returned to the distillation system, a large plate number and high reflux ratio are necessary for the distillation column so as to separate phenols by distillation without mingling of these by-products. Moreover, since removal of these by-products alone by distillation is very difficult, these by-products are gradually accumulated in the distillation system, resulting in degradation of the quality of the product.

SUMMARY OF THE INVENTION

It is a primary object of the present invention to provide a novel process for the preparation of phenols in which the above-mentioned defects and disadvantages can be eliminated and phenols having a high purity can be recovered at a high recovery ratio by subjecting the above-mentioned thermal decomposition product to a preliminary treatment to remove by-products such as mentioned above and then, returning the thermal decomposition product to the distillation system.

More specifically, in accordance with the present invention, there is provided a process for the preparation of phenols which comprises the steps of (I) decomposing a hydroperoxide of an isopropyl aromatic compound with an acid catalyst, (II) separating the decomposition product obtained in step (I) into acetone, phenols, hydrocarbons and distillation residue by distillation of the decomposition product and (III) thermally decomposing the distillation residue and recycling the resulting crude phenol to step (II), wherein the crude phenol obtained in step (III) is contacted with a glycol to form a hydrocarbon layer and an extract layer comprising the glycol and phenol, and the phenol in said extract layer is recycled to step (II).

DETAILED DESCRIPTION OF THE PREFERRED EMBODIMENTS

As is well-known in the art, a hydroperoxide of an isopropyl aromatic compound is obtained by liquid phase oxidation of an isopropyl aromatic compound with molecular oxygen. As the isopropyl aromatic compound, there can be mentioned, for example, cumene, cymene, dimethylcumene and isopropylnaphthalene. Also acid-decomposition of the hydroperoxide of the isopropyl aromatic compound is well-known in the art. Ordinarily, this acid-decomposition is carried out in a solvent such as a ketone or hydrocarbon in the presence of an acid catalyst at a temperature of about 50° to about 80° C.

The acid-decomposition product contains acetone, phenols, unreacted isopropyl aromatic compound, α-methylstyrene and other by-products. Separation of the acid-decomposition product into these components is ordinarily accomplished by distillation conducted after neutralization. At the distillation step, low-boiling-point fractions such as acetone, hydrocarbon fractions such as the isopropyl aromatic compound and α-methylstyrene and phenols are separated. The distillation residue is thermally decomposed to recover phenols and α-methylstyrene.

The operations of distilling the acid-decomposition product and separating it into acetone, phenols, hydrocarbons and distillation residue are known in the art, and as the typical instance, there can be mentioned a distillation process for separation of the acid-decomposition product ordinarily, which comprises the steps of (A) subjecting the acid-decomposition product to distillation to distill off acetone, (B) subjecting the column bottom oil recovered in step (A) to distillation to distill off hydrocarbons, (C) purifying the hydrocarbons from step (B), (D) subjecting the column bottom oil obtained in step (B) to distillation to separate it into a crude phenol and a distillation residue, (E) subjecting the crude phenol from step (D) to extraction distillation using a polyalkylene glycol as an extracting agent to distill off hydrocarbons, and (F) subjecting the column bottom oil obtained in step (E) to distillation to separate it into a phenol and the extracting agent.

The present invention will now be described in detail with reference to the accompanying drawings.

Figure 1:
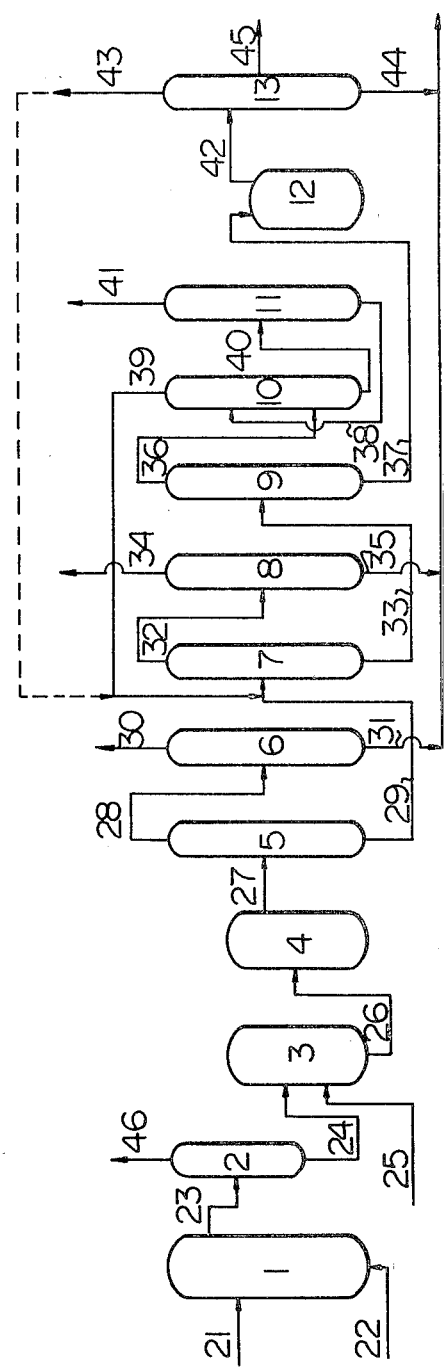
FIG. 1 is a flow sheet illustrating the conventional process for the preparation of phenol from cumene.

Referring to FIG. 1 which is a flow sheet showing the conventional process for preparing phenol from cumene, cumene is fed into an oxidation reactor 1 through a pipe 21 and air is introduced into the reactor 1 through a pipe 22, and in the reactor 1, cumene is oxidized. The oxidation product is fed to a concentration column 2 through a pipe 23, and a part of unreacted cumene is removed by distillation through a pipe 46. The concentrated oxidation product is introduced into an acid-decomposing device 3 through a pipe 24 and is decomposed by an acid catalyst fed through a pipe 25. The acid-decomposition product is fed to a neutralization tank 4 through a pipe 26 and is neutralized and then fed to a crude acetone column 5 through a pipe 27. The acid-decomposition product contains acetone, water, cumene, α-methylstyrene, phenol, acetophenone, tar and the like. In the crude acetone column 5, a fraction having a low boiling point is distilled off from the column head and is fed to an acetone purifying column 6 through a pipe 28. Purified acetone is recovered from the head of the column 6 through a pipe 30. The column bottom oil in the acetone purifying column 6 is discharged through a pipe 31. The column bottom oil in the crude acetone column 5 is fed to a hydrocarbon recovering column 7 through a pipe 29, and hydrocarbons such as cumene and α-methylstyrene and water are distilled off from the column head through a pipe 32. When the recovered distillate is allowed to stand still, it is separated into a hydrocarbon layer and an aqueous layer. The aqueous layer is discarded and the hydrocarbon layer is fed to a hydrocarbon purifying column 8 and cumene and α-methylstyrene are recovered from the column head through a pipe 34. By distillation, α-methylstyrene is isolated, or α-methylstyrene may be converted to cumene by hydrogenation. The column bottom oil in the hydrocarbon purifying column 8 is discharged through a pipe 35. On the other hand, the column bottom oil in the hydrocarbon recovering column 7 is fed to a crude phenol column 9 through a pipe 33 and a tar component is removed in the column 9. The crude phenol distilled off from the head of the column 9 is passed through a pipe 36 and fed into an extraction distillation column 10 to remove hydrocarbons and minute amount components. A polyalkylene glycol having a boiling point much different from that of phenol, such as diethylene glycol or triethylene glycol, is preferred as the extracting agent for extraction distillation. The extracting agent is fed to the extraction distillation column 10 through a pipe 38. Hydrocarbons such as cumene, phenol and by-products are recovered from the head of the extraction distillation column 10, and they are returned to the hydrocarbon recovering column 7 through a pipe 39. The column bottom oil in the extraction distillation column 10 is fed to a phenol purifying column 11 through a pipe 40, and purified phenol coming off from the head of the column 11 is recovered through a pipe 41 and the extracting agent left in the column bottom is recycled to the extraction distillation column 10 through the pipe 38. Incidentally, extraction distillation is not absolutely necessary, but phenol having a high purity can be separated by ordinary distillation. The tar component discharged from the column bottom of the crude phenol column 9 is fed to a thermally decomposing vessel 12 through a pipe 37 and is thermally decomposed in the vessel 12. Thermal decomposition is carried out at a temperature of about 200° to about 300° C. A catalyst may be used, if desired. The oil formed by thermal decomposition is fed to an acetophenone column 13 through a pipe 42, and phenol and hydrocarbons are recovered from the head of the column 13 through a pipe 43 and crude acetophenone is drawn out as a side stream through a pipe 45. The heavy oil is discharged from the bottom of the column 13 through a pipe 44. Acetophenone may be distilled off from the the column head together with phenol. In this case, however, the extraction efficiency at the extraction step described hereinafter is reduced. Therefore, it is preferred that acetophenone be removed as the side stream. The oil formed by thermal decomposition contains many components in addition to phenol. Accordingly, also the crude phenol coming off through the pipe 43 from the acetophenone column contains many by-products. If this crude phenol is returned to the hydrocarbon recovering column 7 and phenol, cumene, α-methylstyrene and the like can be recovered without any trouble, the process will be very convenient. However, as pointed out hereinbefore, the following disadvantages are caused.

More specifically, the above-mentioned crude phenol contains phenylbutenes and 2-methyl-4-phenylpentenes having a boiling point close to that of phenol and other minute amount components causing discoloration in the product phenol. These compounds are fed to the crude phenol column 9 and extraction distillation column 10 together with phenol. In order not to include these compounds in the column bottom stream in the extraction distillation column 10, there should be adopted an operation method in which a considerable amount of phenol is distilled off from the head of the extraction distillation column 10. Since this column head stream is returned to the hydrocarbon recovering column 7, loss of phenol is not caused but the thermal energy necessary for distillation is increased. Furthermore, in this case, the undesirable components are gradually accumulated in the distillation system. Moreover, even if such operation method is adopted, minute amounts of impurity components causing discoloration in the product phenol are introduced into the phenol refining column 11 and mingling of these impurity components into the product phenol cannot be avoided.

The foregoing disadvantages are similarly caused in the process for preparing cresol, xylenol and the like.

One of important features of the present invention is that the crude phenol obtained at the step of thermal decomposition of the distillation residue is contacted with a glycol to separate the extraction residue into a hydrocarbon layer and an extract layer containing the glycol and phenol and the phenol contained in this extract layer is recycled to the above-mentioned step of separating the decomposition product into the respective components by distillation. By this extraction operation using a glycol, the crude phenol is separated completely into two layers, one containing hydrocarbon and the other containing the intended phenol. Furthermore, impurity components having a boiling point close to that of the intended phenol, such as phenylbutenes and 2-methyl-4-phenylpentenes, are substantially completely contained in the hydrocarbon layer together with cumene, α-methylstyrene and the like, and they are hardly transferred into the extract layer containing the intended phenol.

Accordingly, if the phenol in the extract layer is recycled to the above-mentioned distillation separation step, the intended phenol free of the above-mentioned impurity components can be obtained at a high purity and a high recovery ratio. If the separated hydrocarbon layer is recycled to the hydrocarbon purifying column, valuable hydrocarbons such as cumene and α-methylstyrene are recovered from the column head and the above-mentioned impurity components are discharged from the column head. Accordingly, accumulation of the impurity components in the distillation system can be effectively prevented.

Figure 2:
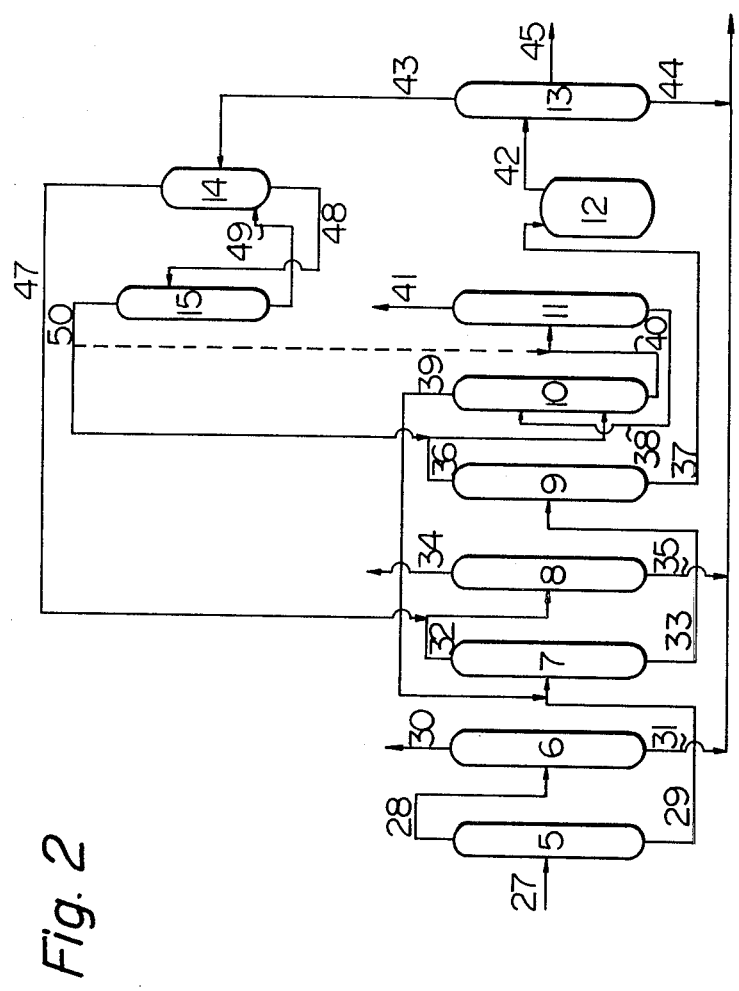
FIG. 2 is a flow sheet illustrating one embodiment of the process for the preparation of phenol according to the present invention.

In one embodiment shown in FIG. 2, the crude phenol recovered from the column head of the above-mentioned acetophenone column 13, which ordinarily comprises 20 to 40% by weight of cumene, 15 to 30% by weight of α-methylstyrene, 0.5 to 5% by weight of phenylbutenes and 2-methyl-4-phenylpentenes and 20 to 40% by weight of the intended phenol, is introduced into an extraction column 14 through a pipe 43 and in this extraction column 14, the crude phenol is contacted with a glycol and is separated into an upper hydrocarbon layer and a lower extract layer comprising the glycol and phenol. The extract layer is fed to a distillation column 15 through a pipe 48, and the phenol distilled from the column head is recycled to the above-mentioned extraction distillation column 10 through a pipe 50.

The column bottom oil in the distillation column 15, that is, the glycol used for extraction, is recycled as the extracting agent to the extraction column 14 through a pipe 49. The hydrocarbon layer separated in the extraction column 14 is recycled to the hydrocarbon purifying column 8 through a pipe 47 and the hydrocarbon layer is separated into valuable hydrocarbons such as cumene and α-methylstyrene and the impurity components. Since the phenol separated at the distillation column 15 has a high purity as shown in Examples given hereinafter, the phenol may be directly fed to the phenol purifying column 11 as indicated by a dot line in FIG. 2 instead of returning the phenol to the extraction distillation column 10.

Figure 3:
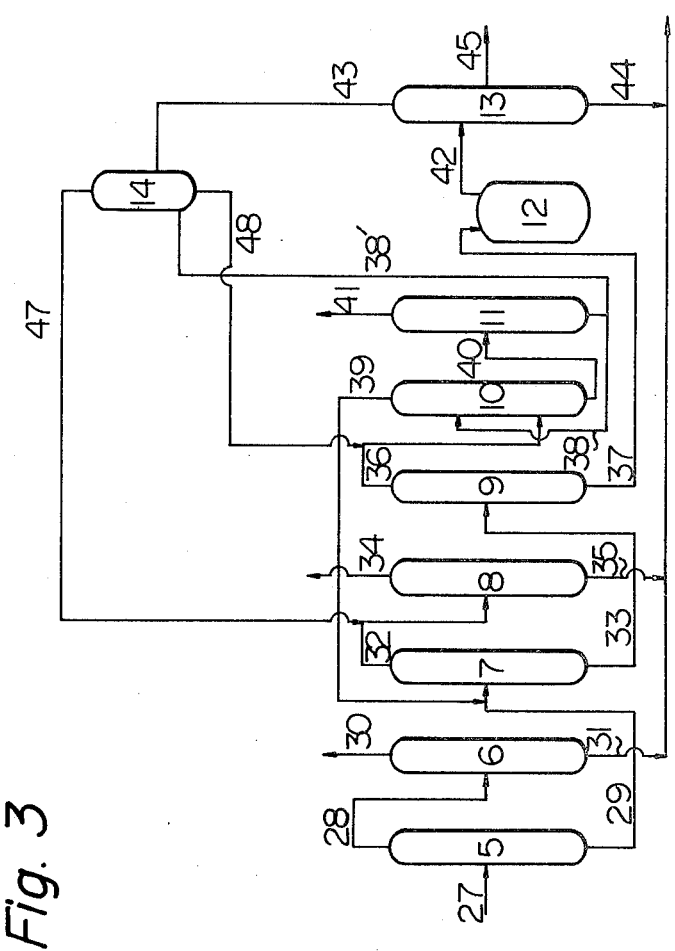
FIG. 3 is a flow sheet illustrating another embodiment of the process for the preparation of phenol according to the present invention.

When the glycol used at the extraction column 14 is the same as the polyalkylene glycol used at the extraction distillation column 10, as shown in FIG. 3, the extract layer containing the polyalkylene glycol and phenol, which is separated at the extraction column, may be fed directly to the extraction distillation column 10 through the pipe 48. A part of the polyalkylene glycol, which is separated as the column bottom oil at the phenol purifying column 11, is recycled as the extraction agent to the extraction column 14 through a pipe 38'.

As the glycol that is used in the present invention, there can be mentioned, for example, alkylene glycols such as ethylene glycol, propylene glycol and isobutylene glycol, and polyalkylene glycols such as diethylene glycol, triethylene glycol and dipropylene glycol. Among these glycols, an alkylene glycol or polyalkylene glycol having a boiling point higher than the boiling point of the intended phenol to be separated, because separation of the phenol from the glycol is remarkably facilitated. It is especially preferred to use a glycol having a boiling point higher by at least 20° C. than that of the intended phenol, as measured under atmospheric pressure. From this viewpoint, it is preferred to use a polyalkylene glycol such as diethylene glycol or triethylene glycol. However, if such polyalkylene glycol is used, the phenol extraction efficiency is relatively low. Accordingly, it is preferred that the polyalkylene glycol be used in combination with water so that the water content in the extracting agent is 10 to 50% by weight, especially 20 to 40% by weight. When the amount of water is too large and exceeds the above range, the ratio of the phenol extracted in the polyalkylene glycol layer is reduced. When water is not used at all or the amount of water is too small, the extraction ratio of the phenol is increased but considerable amounts of the hydrocarbons are extracted in the polyalkylene glycol layer.

The amount used of the glycol to be contacted with the crude phenol is preferably 100 to 300 parts by weight per 100 parts by weight of the crude phenol. The contact is ordinarily carried out at a temperature of about 10° to about 100° C.

The present invention will now be described in detail with reference to the following Examples that by no means limit the scope of the present invention.

EXAMPLE 1

A crude phenol recovered through the pipe 43 from the thermally decomposing device 12 via the acetophenone column 13 was found to have the following composition:

Cumene: 26.8% by weight
α-Methylstyrene: 23.4% by weight
Phenylbutenes and 2-methyl-4-phenylpentenes: 1.4% by weight
Phenol: 27.7% by weight
Other substances: 20.7% by weight An extraction tank equipped with a stirrer and having a capacity of 500 ml was charged with 100 g of the above crude phenol and 200 g of diethylene glycol containing 30% by weight of water, and the crude phenol was violently contacted with the diethylene glycol under agitation while maintaining the temperature in the extraction tank at 30° C. Then, the liquid mixture was allowed to stand still, whereby two layers were formed. The two layers were separated from each other. The upper layer was an extraction residue rich in the hydrocarbons, and the lower layer was an extract composed mainly of phenol and diethylene glycol (DEG). In this case, the phenol extraction ratio was 93%, and the majority of phenol was extracted into DEG. Cumene and α-methylstyrene were left in the extraction residue at ratios of 93% and 92%, respectively. The phenylbutenes and 2-methyl-4-phenylpentenes were recovered substantially completely from the extraction residue and they were not extracted in the DEG layer at all.

Incidentally, the phenol extraction ratio (%) referred to in the instant specification is a value calculated according to the following formula:

$$\text{Phenol extraction ratio (\%)} = \frac{\text{weight (g) of phenol in extract}}{\text{weight (g) of charged phenol}} \times 100$$

EXAMPLES 2 to 4

Extraction was carried out in the same manner as described in Example 1 except that the water content in diethylene glycol used as the extracting agent was changed to 10, 20 or 40% by weight and the extracting agent/crude phenol weight ratio was changed to 3/2. The crude phenol used in the extraction experiment was found to have the following composition:

Cumene: 28.7% by weight
α-Methylstyrene: 24.8% by weight

Phenylbutenes and 2-methyl-4-phenylpentenes: 1.4% by weight

Phenol: 28.7% by weight

Other substances: 16.4% by weight

Results obtained in this extraction experiment are summarized in Table 1.

TABLE 1

| | Water Content (% by weight) in Diethylene Glycol | | |
|---|---|---|---|
| | 10 | 20 | 40 |
| Phenol extraction ratio (%) | 97 | 97 | 93 |
| Cumene residual ratio* (%) | 83 | 92 | 99 |
| α-Methylstyrene residual ratio* (%) | 81 | 89 | 98 |
| Residual ratio* (%) of phenylbutenes and 2-methyl-4-phenylpentenes | 95 | 100 | 100 |

Note
The residual ratio* (%) of each component is a value calculated according to the following formula:

$$\text{The residual ratio (\%)} = \frac{\text{weight (g) of component in extraction residue}}{\text{weight (g) of charged component}} \times 100$$

EXAMPLE 5

The extraction experiment was carried out in the same manner as in Examples 2 to 4 except that triethylene glycol containing 20% by weight of water was used as the extracting agent.

The phenol extraction ratio was 97%, and cumene and α-methylstyrene were left in the extraction residue at ratios of 91% and 87%, respectively.

The phenylbutenes and 2-methyl-4-phenylpentenes were left substantially completely in the extraction residue and they were not extracted in the triethylene glycol layer at all.

EXAMPLE 6

The extraction experiment was carried out in the same manner as described in Example 1 by using 150 g of the crude phenol used in Examples 2 to 4 and 150 g of ethylene glycol.

The phenol extraction ratio was 92%, and cumene and α-methylstyrene were left in the extraction residue at ratios of 97% and 96%, respectively.

The phenylbutenes and 2-methyl-4-phenylpentenes were left substantially completely in the extraction residue.

What is claimed is:

1. In a process for the preparation of phenols which comprises the steps of (I) decomposing a hydroperoxide of an isopropyl aromatic compound selected from the group consisting of cumene, cymene, dimethylcumene and isopropyl naphthalene in a ketone or hydrocarbon solvent in the presence of an acid catalyst at a temperature of about 50° to 80° C., (II) distilling the decomposition product obtained in step (I) to separate the decomposition product into acetone, phenols, hydrocarbons and distillation residue, and (III) thermally decomposing the distillation residue at a temperature of about 200° to about 300° C. and recycling the crude phenol to step (II), the improvement which comprises contacting the crude phenol obtained in step (III) with a glycol in an amount of 100 to 300 parts by weight per 100 parts by weight of the crude phenol at a temperature of 10° to 100° C. to separate the crude phenol into an upper hydrocarbon layer and a lower extract layer comprising the glycol and phenol, and recycling the phenol in said extract layer to step (II).

2. A process according to claim 1 wherein the glycol is an alkylene glycol having a boiling point higher than that of the phenol.

3. A process according to claim 1 wherein the glycol is a polyalkylene glycol having a boiling point higher than that of the phenol.

4. A process according to claim 1 wherein the glycol is a polyalkylene glycol and the crude phenol is contacted with the polyalkylene glycol containing 10 to 50% by weight of water.

5. A process according to claim 1, wherein step (II) of the distillation of the decomposition product comprises the steps of (A) subjecting the acid-decomposition product to distillation to distill off acetone, (B) subjecting the column bottom oil recovered in step (A) to distillation to distill off hydrocarbons, (C) purifying the hydrocarbons from step (B), (D) subjecting the column bottom oil obtained in step (B) to distillation to separate the same into a crude phenol and a distillation residue, (E) subjecting the crude phenol from step (D) to extraction distillation using a polyalkylene glycol as an extracting agent to distill off hydrocarbons, and (F) subjecting the column bottom oil obtained in step (E) to distillation to separate the same into a phenol and the extracting agent, and said extract layer is subjected to distillation to separate the same into a phenol fraction and glycol, and the phenol fraction is recycled to step (E) or (F).

6. A process according to claim 5 wherein said hydrocarbon layer is recycled to step (C).

* * * * *